United States Patent
Schober et al.

(10) Patent No.: US 9,375,305 B2
(45) Date of Patent: Jun. 28, 2016

(54) STRUCTURE MODELED ON A BIOLOGICAL TISSUE AND METHOD FOR PRODUCING SAID STRUCTURE

(75) Inventors: Andreas Schober, Erfurt (DE); Michael Gebinoga, Ilmenau (DE); Uta Fernekorn, Erfurt (DE); Frank Weise, Ilmenau (DE); Jörg Hampl, Erfurt (DE); Julia Katzmann, Wutha-Farnroda (DE); Thomas Klar, Linz (AT)

(73) Assignee: TECHNISCHE UNIVERSITAET ILMENAU, Ilmenau (DE)

( * ) Notice: Subject to any disclaimer, the term of this patent is extended or adjusted under 35 U.S.C. 154(b) by 0 days.

(21) Appl. No.: 13/877,721

(22) PCT Filed: Sep. 30, 2011

(86) PCT No.: PCT/EP2011/067177
§ 371 (c)(1),
(2), (4) Date: Apr. 4, 2013

(87) PCT Pub. No.: WO2012/045688
PCT Pub. Date: Apr. 12, 2012

(65) Prior Publication Data
US 2013/0197668 A1   Aug. 1, 2013

(30) Foreign Application Priority Data
Oct. 5, 2010 (DE) .......................... 10 2010 037 973
Oct. 13, 2010 (DE) .......................... 10 2010 038 155

(51) Int. Cl.
| | |
|---|---|
| G01N 33/48 | (2006.01) |
| G01N 33/50 | (2006.01) |
| A61F 2/02 | (2006.01) |
| G05B 19/4099 | (2006.01) |
| G06F 19/24 | (2011.01) |
| G06F 19/12 | (2011.01) |

(52) U.S. Cl.
CPC .............. *A61F 2/02* (2013.01); *G05B 19/4099* (2013.01); *G05B 2219/49019* (2013.01); *G05B 2219/49031* (2013.01); *G06F 19/12* (2013.01); *G06F 19/24* (2013.01)

(58) Field of Classification Search
None
See application file for complete search history.

(56) References Cited

U.S. PATENT DOCUMENTS
| | | | |
|---|---|---|---|
| 4,665,492 A | 5/1987 | Masters | |
| 6,139,574 A | 10/2000 | Vacanti et al. | |
| 6,197,575 B1 | 3/2001 | Griffith et al. | |
| 6,649,162 B1 | 11/2003 | Biering et al. | |
| 2005/0169962 A1 | 8/2005 | Bhatia et al. | |

FOREIGN PATENT DOCUMENTS
| | | |
|---|---|---|
| DE | 101 52 878 | 5/2003 |
| DE | 696 24 241 | 6/2003 |
| DE | 699 03 800 | 10/2003 |
| DE | 697 24 243 | 6/2004 |
| WO | 03/037606 | 5/2003 |

OTHER PUBLICATIONS

X-rays, 2003, 2 pages. Macmillan Encyclopedia. Retreived online on Dec. 27, 2003 from <<http://www.credoreference.com>>.*
Heckel, et al., "An Anticoagulant With Light-Triggered Anidote Activity", Angewandte Chemie Int. Ed., vol. 45, pp. 6748-6750 (2006). (3 pages total).
Linke, K., et al., "Engineered Liver-Like Tissue on a Capillarized Matrix for Applied Research", Tissue Engineering, vol. 13, No. 11, pp. 2699-2707 (2007). (9 pages total).
Ott, C., et al., "Regeneration and Orthotopic transplantation of a bioartificial lung", Nature Medicine, vol. 16, pp. 927-933 (2010). (8 pages total).
Kim, Y., et al., "Using photons to manipulate enzyme inhibition by an azobenzene-modified nucleic acid probe", PNAS, vol. 106, No. 16, pp. 6489-6494, (2009). (6 pages total).
Ananda, S., et al.: "The visualization of hepatic vasculature by X-ray micro-computed tomography" in the Journal of Electron Microscopy, vol. 55(3), 2006, pp. 151-155.
Chan, V., et al.: "Three-dimensional photo-pattering of hydrogels using stereolitography for long-term cell encapsulation" in Lab on a Chip, 2010, vol. 10, pp. 2062-2070.
Claeyssens, F., et al.: "Three-Dimensional Biodegradable Structures Fabricated by Two-Photon Polymerization" in Langmuir 2009, Edition 25, pp. 3219-3223.
Hsieh, T. M.: "Three-dimensional microstructured tissue scaffolds fabricated by two-photon laser scanning photolithography" in Biomaterials, 2010, accepted for publication on Jun. 22, 2010, pp. 1-5.
Liu, V. A.: "Three-dimensional Photopatterning of Hydrogels Containing Living Cells" in Biomedical Microdevices 4:4, 2002, pp. 257-266.

(Continued)

*Primary Examiner* — Russell S Negin
(74) *Attorney, Agent, or Firm* — Ann Wieczorek; Mayer & Williams PC

(57) ABSTRACT

The present invention relates to a method for producing a structure modeled on a biological tissue. The invention also relates to a structure which can be produced using the method according to the invention. According to an embodiment of the invention, a precursor of a biopolymer is locally irradiated with electromagnetic radiation in a targeted manner, wherein the irradiation, in particular the selection of the areas to be irradiated, is effected according to data which describe a structural construction at least components of the extracellular matrix of the biological tissue. In this case, the electromagnetic radiation is such that two-photon or multi-photon absorption takes place in the irradiated areas of the precursor and results in the precursor being polymerized to form the biopolymer in the irradiated areas, with the result being that the precursor is at least partially solidified there.

6 Claims, No Drawings

(56) References Cited

OTHER PUBLICATIONS

Tsang, V. L.: "Fabrication of 3D hepatic tissue by additive photopatterning of cellular hydrogels" in The FASEB Journal, vol. 21, 2007, pp. 790-801.

Weiss, T. et al., "Two-Photon Polymerization for Microfabrication of Three-Dimensional Scaffolds for Tissue Engineering Application" in O. Gössel, W. C. Schlegel, WC 2009, IFMBE Proceeding 25/X, pp. 140-142, 2009.

International Search Report mailed on Dec. 29, 2011 in connection with corresponding International Application No. PCT/EP2011/067177 (2 pages total).

* cited by examiner

STRUCTURE MODELED ON A BIOLOGICAL TISSUE AND METHOD FOR PRODUCING SAID STRUCTURE

FIELD OF THE INVENTION

The present invention relates to a method for producing a structure modeled on a biological tissue. In this case, an extracellular matrix of the biological tissue is modeled, in particular, with the result that biological cells can be introduced into the modeled extracellular matrix in order to be able to model the entire biological tissue. The invention further relates to a structure which can be produced using the method according to the invention, and which is used to model at least one extracellular matrix of a biological tissue. A modeled biological tissue represents a further subject matter of the invention.

BACKGROUND OF THE INVENTION

The article by Weiss, T. et al., "Two-Photon Polymerization for Microfabrication of Three-Dimensional Scaffolds for Tissue Engineering Application" in O. Gössel, W. C. Schlegel, WC 2009, IFMBE Proceeding 25/X, pp 140-142, 2009, describes three-dimensional structures in which biological cells can be embedded. The structures consist of a biocompatible photopolymer, for example, L-lactid-ε-caprolactone, which is polymerized by two-photon polymerization. One structure, shown by way of example, has a regular geometric shape, referred to as a woodpile structure.

The article by Claeyssens, F., et al.: "Three-Dimensional Biodegradable Structures Fabricated by Two-Photon Polymerization" in Langmuir 2009, Edition 25, pp 3219-3223, describes the production of three-dimensional structures from biocompatible polymers on the basis of two-photon polymerization.

The article by Chan, V., et al.: "Three-dimensional photopatterning of hydrogels using stereolitography for long-term cell encapsulation" in Lab on a Chip, 2010, Volume 10, pp 2062-2070, describes a method for polymerizing hydrogels, for which the light from a UV laser is used. The polymerized hydrogels form structures for cells.

From the article by Hsieh, T. M.: "Three-dimensional microstructured tissue scaffolds fabricated by two-photon laser scanning photolithography" in Biomaterials, 2010, accepted for publication on 22 Jun. 2010, assays for testing the biocompatibility of a polymer structured by a two-photon process are known.

From the article by Tsang, V. L.: "Fabrication of 3D hepatic tissue by additive photopatterning of cellular hydrogels" in The FASEB Journal, Volume 21, 2007, pp 790-801, a method for producing three-dimensional tissue structures on the basis of photopolymerizable hydrogels is known. Photopolymerization is carried out using a UV light source. Material which remains unbonded after photopolymerization is flushed out.

The article by Liu, V. A.: "Three-dimensional Photopatterning of Hydrogels Containing Living Cells" in Biomedical Microdevices 4:4, 2002, pp 257-266, describes the production of three-dimensional structures by photopolymerization of hydrogels.

From the article by Ananda, S., et al.: "The visualization of hepatic vasculature by X-ray micro-computed tomography" in the Journal of Electron Microscopy, Volume 55(3), 2006, pp 151-155, a method for three-dimensional tomography of blood vessels is known.

The article by Heckel, et al.: "An Anticoagulant With Light-Triggered Anidote Activity" in Angewandte Chemie Int. Ed., Volume 45, 2006, pp 6748-6750, and the article by Kim, Y., et al.: "Using photons to manipulate enzyme inhibition by an azobenzene-modified nucleic acid probe" in PNAS, Volume 106, No. 16, 2009, pp 6489-6494, describe photoactivable thrombin inhibitors.

The article by Linke, K., et al.: "Engineered Liver-Like Tissue on a Capillarized Matrix for Applied Research" in Tissue Engineering, Volume 13, No. 11, 2007, pp 2699-2707, and the article by Ott, C., et al.: "Regeneration and Orthotopic transplantation of a bioartificial lung" in Nature Medicine, Volume 16, 2010, pp 927-933, describe the colonization of extracellular matrices with new cells.

WO 03/037606 A1 describes a method for generating three-dimensional bodies or surfaces by laser irradiation. In this method, polymerization is implemented via two-photon absorption.

From DE 699 03 800 T2, vascularized, perfused arrangements for microtissues and microorgans are known, which preferably consist of a biocompatible polymer and have open channels for nutrients and oxygen.

DE 696 24 241 T2 describes a method for producing matrices for vascularized tissue regeneration, in which pores for colonization with cells and cavities with openings for connections to channels in the tissue of a patient are formed.

From DE 697 24 243 T2, a hemostatic sponge having a collagen base is known, which contains thrombin or a precursor of thrombin.

DE 101 52 878 A1 describes a method for producing three-dimensional bodies or surfaces from organopolysiloxane-containing starting materials, in which two-photon or multi-photon polymerization takes place.

SUMMARY OF THE INVENTION

The problem addressed by the present invention is that of improving the modeling of biological tissues over that of the prior art, for which purpose structures and methods for producing said modeling are to be provided, which will enable adequate conditions for the colonization of biological cells.

The stated problem is solved by a method according to the attached claim 1. The problem is further solved by a structure according to the attached dependent claim 10.

DETAILED DESCRIPTION OF THE INVENTION

The method according to the invention is used for producing a structure modeled on a biological tissue. The structure to be produced forms at least one extracellular matrix, which represents a modeling of the extracellular matrix of the biological tissue. However, the structure to be produced can also represent a complete modeling of the biological tissue, and therefore, it involves an at least partially synthetically produced tissue. In any case, the structure to be produced is suitable for the colonization of biological cells therein, and for allowing said cells to execute the functions there that characterize life.

In a first step of the method according to the invention, data are provided which describe a structural construction at least of components of the extracellular matrix of the biological tissue. The data describe the geometry of the extracellular matrix, at least to the extent to which the extracellular matrix of the biological tissue is to be modeled. The data describe the geometric shape of the extracellular matrix, wherein different types of components of the extracellular matrix can each be separately described. Description involves the specification of contiguous partial quantities for a plane or for the space, wherein as the mathematical mean, for example, analytical data in the form of a curve function or planar function or the direct definition of a partial quantity of a plane or of the space are suitable. The data preferably describe the structural construction of the entire extracellular matrix, i.e., the geometry of all components of the extracellular matrix. These data are provided, for example, by accessing the results of previous analyses of corresponding biological tissues. The data can also be provided by analyzing the biological tissue to be modeled using a tomographic process.

In a further step of the method according to the invention, a precursor of a biopolymer is provided. The precursor is a starting material in the sense of a precursor of the biopolymer, for example, in the form of a monomer. The biopolymer is a polymer which is at least biocompatible and is preferably provided as a bio-based polymer, particularly as a native biopolymer. According to the invention, the precursor is locally irradiated with electromagnetic radiation in a targeted manner, wherein the irradiation, in particular, the selection of the areas to be irradiated, is effected according to the structural construction described by the data. In other words, precisely the contiguous partial quantities of the plane or of the space which are defined by the data are irradiated. The electromagnetic radiation can be formed by a focused light or by a laser beam, for example. According to the invention, the electromagnetic radiation is such that two-photon or multi-photon absorption takes place in the irradiated areas of the precursor, and results in the precursor being polymerized in the irradiated areas to form the biopolymer, so that the precursor is at least partially solidified there. Since the precursor is irradiated locally in a targeted manner according to the structural construction described by the data, the biopolymer that forms is configured with a structure on which the extracellular matrix of the biological tissue is modeled. The polymerized biopolymer represents an at least partially solidified body, the planar and/or spatial extension of which is at least partially equivalent to the planar or spatial extension of the extracellular matrix of the biological tissue to be modeled.

One particular advantage of the method according to the invention consists in that the structure that can be produced with this method is matched in terms of its geometry and its structural construction to the extracellular matrix of the biological tissue being modeled, and as a result, the living conditions offered by the structure for the corresponding biological cells are substantially improved over those of the prior art.

The data preferably describe the extracellular matrix of the biological tissue three-dimensionally, and therefore, the data describe the structural construction of the extracellular matrix in its spatial configuration. In this embodiment of the method according to the invention, therefore, the local irradiation of the precursor with the electromagnetic radiation in a targeted manner is carried out according to the structural construction described three-dimensionally by the data, and therefore, the formed biopolymer is formed three-dimensionally by the irradiation. The structure modeled by the biopolymer is modeled in the spatial-geometric properties of the extracellular matrix of the biological tissue to be modeled.

The structural construction of the extracellular matrix is described by the data at least to the extent that geometric formations, for example, cavities in which biological cells can colonize, are defined. Furthermore, the data preferably describe the arrangement of channels to function as vessels in the extracellular matrix of the biological tissue. The vessels serve, for example, to transport fluids, such as blood, nutrient solution, or water within the biological tissue, wherein the vessels are provided in the structure to be modeled for the respectively same purpose. The vessels serve particularly to supply the biological cells in the biological tissue or in the modeled structure. In this embodiment of the method according to the invention, the arrangement of the vessels, preferably the spatial configuration of the vessels in the extracellular matrix of the biological tissue, matches the arrangement or the spatial configuration of vessels which result from the polymerization of the precursor in the solidified biopolymer.

The data preferably further describe the arrangement of those vessels in the extracellular matrix of the biological tissue, which are embodied as capillaries. Accordingly, the structure to be produced also has those vessels which are embodied as capillaries and are of particular importance for supplying fluids to biological cells to be received.

The biological tissue described by the data is preferably animal or human. Therefore, the method according to the invention is used to model human or animal tissue.

The biological tissue described by the data is preferably formed as an organ of an animal or a human, and therefore, the method according to the invention is used for modeling a human or animal organ. The organ can be, for example, a liver, a kidney or a spleen. In such cases, the data describe, for example, the extracellular matrix of a liver, particularly the vessels present in the liver through which the liver cells are incorporated into the circulatory system.

In one particularly preferred embodiment of the method according to the invention, fibrinogen is provided as the precursor of the biopolymer fibrin. In this embodiment of the method according to the invention, fibrinogen polymerizes to fibrin, as is also the case in biological processes, particularly with blood clotting. Within the scope of the invention, it was unexpectedly found that this polymerization can also be triggered by two-photon or multi-photon absorption or by two-photon or multi-photon excitation, for which purpose the fibrinogen must be irradiated with a corresponding amount of electromagnetic radiation. Fibrinogen or Factor I is a soluble glycoprotein having a high molecular weight of approximately 340 kDal, which is present in blood plasma. It consists of three non-identical pairs of polypeptide chains (Aα, Bβ, γ)$_2$, which are linked by covalent disulfide bridges. The amino-terminal regions of the six polypeptides are arranged in close proximity via disulfide bridges, whereas the carboxyl ends are spaced farther apart. The A- and B-parts of the Aα and Bβ chains are the fibrinopeptides A and B, which have a surplus of negative charges. This facilitates the solubility of fibrinogen in plasma, and, as a result of electrostatic repulsion, also prevents an aggregation of fibrinogen molecules. The conversion of soluble fibrinogen to polymeric fibrin is one of the most important steps in blood clotting and is ordinarily catalyzed by thrombin. Thrombin as a serine protease cleaves the small fibrinopeptides A and B (16 and 14 amino acids, respectively) from the high-molecular fibrinogen. As a result, binding sites are exposed, which allow the molecule, now called fibrin, to congregate spontaneously to form long-chain polymers. This aggregation is also promoted by the elimination of the surplus of negative charges. Subsequent links between the amide group of glutamines and the ε-amino group of lysines by a transglutaminase leads to a cross-linking of the already polymerized fibrin fibers to a more stable entity, called a thrombus. In this embodiment of the method according to the invention, this polymerization of the soluble fibrinogen to the thrombus stabilized via cross-linking, which is initialized and terminated by a complex enzyme cascade, can be carried out entirely non-enzymatically on the basis of the fibrinogen. Therefore, this embodiment of the method according to the invention is preferably carried out enzyme-free, particularly without the presence of thrombin, whereas the natural biological process requires the enzyme thrombin. This embodiment of the method according to the invention is preferably carried out at least in the absence of one or more of the enzymes necessary for biological polymerization. The first formation of the long-chain polymers is carried out by means of two-photon or multi-photon polymerization in the described manner. The subsequent bonding of glutamines and lysines via transglutaminase is preferably implemented via chemical bonding, particularly preferably in that the provided fibrinogen or the fibrin fibers polymerized following irradiation are made to react with DSS, DSP, DTSSP and/or sulfo-NHS-SS-biotin, in order to modify amino groups of the fibrinogen or the fibrin fibers, thereby stabilizing the structure of the fibrin fibers such that a thrombus is produced. The stated chemical bonding possibilities are described in the context of the stabilization of collagen below.

In an alternative, particularly preferred embodiment of the method according to the invention, collagen is provided as the precursor of the polymer formed from polymerized collagen. The collagen, which is preferably formed from native collagen, also polymerizes like fibrinogen as a result of two-photon or multi-photon absorption or two-photon or multi-photon excitation, which is effected using a corresponding amount of electromagnetic radiation. Contrary to the natural process, no cross-linking agent is required for this purpose, and therefore, this embodiment of the method according to the invention is preferably carried out in the absence of cross-linking agents or preferably at least in the partial absence of cross-linking agents.

The collagen to be provided preferably has a triple-helix structure with a peptide sequence -Gly-Xaa-Yaa- in a primary structure having at least one fraction of prolinein the Xaa position and at least one fraction of hydroxyprolinein the Yaa position. Collagen of this type is suitable for polymerizing to a biocompatible polymer.

The polymerized collagen preferably forms fibrils, with which the structure modeled on the extracellular matrix is reinforced.

The provided collagen further preferably has covalently bonded polyethylene glycol groups having the composition —O—(CH$_2$CH$_2$—O—)$_n$ with $2 \leq n \leq 400$, with which the structure of the collagen is stabilized.

The provided collagen is preferably made to react with 2-bromoethylamines, ethyleneimines, N-(β-iodoethyl)trifluoroacetamide and/or 2-aminoethyl-2'-aminoethanethiolsulfonates, in order to modify sulfhydryl groups of the collagen, thereby stabilizing the structure of the collagen.

The provided collagen is preferably made to react with disuccinimidyl suberate (DSS); dithiobis[succinimidyl propionate](DSP); synonym 3,3'-dithio-bis-(3-sulfo-N-hydroxysuccinimidylpropionate) disodium (DTSSP) and/or sulfosuccinimidyl 2-(biotinamido)-ethyl-1,3-dithiopropionate (sulfo-NHS-SS-biotin), for the purpose of modifying amino groups of the collagen, thereby stabilizing the structure of the collagen.

The precursor can be provided in various forms. For example, the precursor can be provided as a diluted solution or as a diluted, buffered solution in an aqueous medium. The precursor can also be provided as a diluted solution in a non-aqueous medium. Alternatively, the precursor is preferably provided in a dry state as a powder or as a film. The precursor, particularly the collagen, is preferably provided in concentrated form, as a gel-like substance or as a substance that is solidified by drying a diluted solution or a concentrated solution.

In one particular embodiment of the method according to the invention, the precursor, particularly the fibrinogen, is provided in a mixture which comprises biological cells of the same type as cells of the biological tissue to be modeled. In this embodiment of the method according to the invention, the modeled structure, particularly the modeled extracellular matrix, already contains biological cells, and therefore, the biological tissue is already modeled in parts or in its entirety.

The data are preferably provided by analyzing the biological tissue to be modeled using a three-dimensional tomographic process. In the analysis of the biological tissue by the three-dimensional tomographic process, the three-dimensional structure of the vessels is particularly determined.

In one preferred embodiment of the method according to the invention, the electromagnetic radiation is harmless to cells that are of the same type as cells of the biological tissue. More particularly, no radiation in the UV range is used. Therefore, the cells can be located at the site of the structure to be formed during irradiation of the precursor, without being destroyed by the irradiation. With this embodiment of the method according to the invention, living cells can be located in the structure modeled on the extracellular matrix, so that the biological tissue is modeled in part or in its entirety. The electromagnetic radiation is preferably formed by red or infrared light, which is harmless to many cells.

The electromagnetic radiation is particularly preferably focused on the regions of the precursor to be irradiated, in order to ensure the locally selective irradiation of the precursor. The focused electromagnetic radiation permits a three-dimensional structuring of the biopolymer to be polymerized.

The electromagnetic radiation is preferably formed by a beam from a laser. The laser beam can be directed locally precisely onto the precursor in a targeted manner. The laser beam is particularly preferably focused, for example, with the help of an imaging lens.

In a further preferred embodiment of the method according to the invention, fractions of the precursor which are not polymerized after irradiation are flushed out. In flushing, cavities, etc. which are provided for receiving biological cells are emptied.

In one particular embodiment of the method according to the invention, an advanced structuring of the polymerized biopolymer is carried out by means of a local irradiation of the polymerized biopolymer with destructive electromagnetic radiation in a targeted manner, wherein the destructive electromagnetic radiation is such that it destroys the polymerization in the irradiated regions of the polymerized biopolymer.

One particularly preferred embodiment of the method according to the invention is further designed for producing a tissue modeled on the biological tissue, for which purpose said method further comprises a step in which biological cells are flushed into the structure modeled on the extracellular matrix of the biological tissue. The biological cells are similar in type to cells of the biological tissue to be modeled. This embodiment of the method according to the invention enables the technical production of a biological tissue, for example, in the form of a human or animal organ.

A further subject matter of the invention involves a structure which is modeled on an extracellular matrix of a biological tissue and can be produced with the help of the method according to the invention.

A tissue which can be produced by an embodiment of the method according to the invention provided for producing a tissue represents a further subject matter of the invention. This tissue can be in the form of a complete human or animal organ.

The invention claimed is:
1. A method for producing a structure modeled on a biological tissue, comprising the following steps:
 (a) providing data which describe a structural construction in a three-dimensional configuration of at least compo- nents of an extracellular matrix of the biological tissue, wherein the data describe the spatial configuration of vessels in the extracellular matrix of the biological tissue;

(b) providing a precursor of a biopolymer; and (c) using electromagnetic radiation to produce the structure wherein electromagnetic radiation is used to locally irradiate the precursor in a targeted manner according to the structural construction described by the data, wherein the electromagnetic radiation is such that two-photon or multi-photon absorption takes place in the irradiated areas of the precursor, by which the precursor is polymerized to the biopolymer in the irradiated areas and the biopolymer formed from such irradiated precursor is embodied with a structure modeled on the geometry of the extracellular matrix of the biological tissue, and wherein the polymerized biopolymer represents an at least partially solidified body, the spatial extension of which is equivalent to the spatial extension of the extracellular matrix of the biological tissue being modeled, and wherein the spatial configuration of the vessels in the extracellular matrix of the biological tissue matches the spatial configuration of vessels which result from the polymerization of the precursor in the solidified biopolymer.

2. The method according to claim 1, wherein the data are provided such that the biological tissue is analyzed using a three-dimensional tomographic process.

3. The method according to claim 1, wherein fibrinogen is provided as the precursor of the biopolymer fibrin.

4. The method according to claim 1, wherein collagen is provided as the precursor of the polymer formed from polymerized collagen.

5. The method according to claim 1, further comprising the following step for the advanced structuring of the polymerized biopolymer:

(d) locally irradiating the polymerized biopolymer with destructive electromagnetic radiation in a targeted manner, wherein the destructive electromagnetic radiation is such that it destroys polymerization in the irradiated areas of the polymerized biopolymer.

6. The method according to claim 1, wherein a tissue modeled on the biological tissue is produced and wherein the method further comprises the following step:

(e) flushing cells into the structure modeled on the extracellular matrix of the biological tissue, the type of said cells matching the cells of the biological tissue.

* * * * *